US012779140B2

(12) United States Patent
Traverso et al.

(10) Patent No.: US 12,779,140 B2
(45) Date of Patent: Nov. 3, 2026

(54) DISPENSING DEVICE WITH MEMBRANE BASED TRIGGER

(71) Applicant: Massachusetts Institute of Technology, Cambridge, MA (US)

(72) Inventors: Carlo Giovanni Traverso, Newton, MA (US); Graham Arrick, Cambridge, MA (US); Torben Sebastian Last, Sollentuna (SE)

(73) Assignee: Massachusetts Institute of Technology, Cambridge, MA (US)

( * ) Notice: Subject to any disclaimer, the term of this patent is extended or adjusted under 35 U.S.C. 154(b) by 1010 days.

(21) Appl. No.: 17/782,355

(22) PCT Filed: Dec. 11, 2020

(86) PCT No.: PCT/US2020/064550
§ 371 (c)(1),
(2) Date: Jun. 3, 2022

(87) PCT Pub. No.: WO2021/119452
PCT Pub. Date: Jun. 17, 2021

(65) Prior Publication Data

US 2023/0027746 A1 Jan. 26, 2023

Related U.S. Application Data

(60) Provisional application No. 62/948,118, filed on Dec. 13, 2019.

(51) Int. Cl.
*A61M 5/44* (2006.01)

(52) U.S. Cl.
CPC ....... *A61M 5/44* (2013.01); *A61M 2205/3673* (2013.01)

(58) Field of Classification Search
CPC ............................ A61M 2205/20; A61M 5/44
See application file for complete search history.

(56) References Cited

U.S. PATENT DOCUMENTS 8,442,611 B2 5/2013 Santini, Jr. et al.
2004/0024382 A1* 2/2004 Cho .................... A61M 31/002 604/891.1
2009/0308752 A1* 12/2009 Evans ................... A61M 5/145 204/627
2013/0274665 A1* 10/2013 Lu ........................... A61M 5/14 604/113

(Continued)

OTHER PUBLICATIONS

International Search Report and Written Opinion mailed Mar. 4, 2021, for Application No. PCT/US2020/064550.

(Continued)

*Primary Examiner* — Bradley J Osinski
(74) *Attorney, Agent, or Firm* — Wolf, Greenfield & Sacks, P.C.

(57) ABSTRACT

A device may be configured with a housing having a reservoir and an outlet separated by a heat rupturable membrane. The membrane may serve to separate a material held within the reservoir from the outlet until the membrane is ruptured. The membrane may include a heater configured to selectively rupture the membrane when actuated. The heater may be physically removed and/or thermally insulated from at least one of an environment surrounding the device and the reservoir.

22 Claims, 12 Drawing Sheets

(56) References Cited

U.S. PATENT DOCUMENTS

| | | | |
|---|---|---|---|
| 2017/0119960 | A1 | 5/2017 | Dang et al. |
| 2019/0060218 | A1 | 2/2019 | Chen et al. |
| 2022/0080115 | A1 | 3/2022 | Traverso et al. |
| 2022/0175681 | A1 | 6/2022 | Traverso et al. |
| 2022/0257855 | A1 | 8/2022 | Traverso et al. |
| 2022/0280435 | A1 | 9/2022 | Traverso et al. |
| 2023/0050912 | A1 | 2/2023 | Traverso et al. |

OTHER PUBLICATIONS

International Preliminary Report on Patentability mailed Jun. 23, 2022, for Application No. PCT/US2020/064550.

Abramson et al., An ingestible self-orienting system for oral delivery of macromolecules. Science. Feb. 8, 2019;363(6427):611-615.

Kong et al., 3D-Printed Gastric Resident Electronics. Adv Mater Technol. 2019;4(3):1800490. doi: 10.1002/admt.201800490. Epub Dec. 13, 2018.

Li et al., A low power, on demand electrothermal valve for wireless drug delivery applications. Lab Chip. Jan. 7, 2010;10(1):101-10. doi: 10.1039/b910248e. Epub Oct. 19, 2009.

* cited by examiner

DISPENSING DEVICE WITH MEMBRANE BASED TRIGGER

RELATED APPLICATIONS

This application is a national stage filing under 35 U.S.C. § 371 of International application serial number PCT/US2020/064550, filed Dec. 11, 2020, which claims priority under 35 U.S.C. 119(e) to U.S. provisional application Ser. No. 62/948,118, filed Dec. 13, 2019, the disclosure of each of which is incorporated herein by reference in its entirety for all purposes.

FIELD

Disclosed embodiments relate to dispensing devices having a membrane based trigger including, for example, a heat rupturable membrane.

BACKGROUND

Certain therapeutics are composed of large and complex molecules that denature readily when administered via the oral-gastrointestinal (GI) route. Accordingly, patients who need these therapeutics typically use more invasive forms of drug administration that are outside the GI route including, for example, subcutaneous injection.

BRIEF SUMMARY

According to one aspect, a device for dispensing a material includes a housing including a reservoir and an outlet, wherein the reservoir is configured to contain the material; a heat rupturable membrane disposed within the housing and configured to selectively separate the reservoir from the outlet; and a heater thermally coupled to the heat rupturable membrane and thermally insulated from at least one of an environment surrounding the device and the reservoir.

According to another aspect, a thermally actuated valve includes a frame; a heat rupturable membrane disposed in an opening in the frame; and a heater disposed within the frame and thermally coupled to the heat rupturable membrane, wherein the heater is configured to rupture the heat rupturable membrane when actuated.

According to a further aspect, a method of dispensing a material is disclosed. The method includes heating a heat rupturable membrane with a heater thermally insulated from at least one of an external environment of a device and a reservoir of the device; rupturing the heat rupturable membrane; and dispensing the material from the reservoir through an outlet of the device after the heat rupturable membrane is ruptured.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

Figure 1:
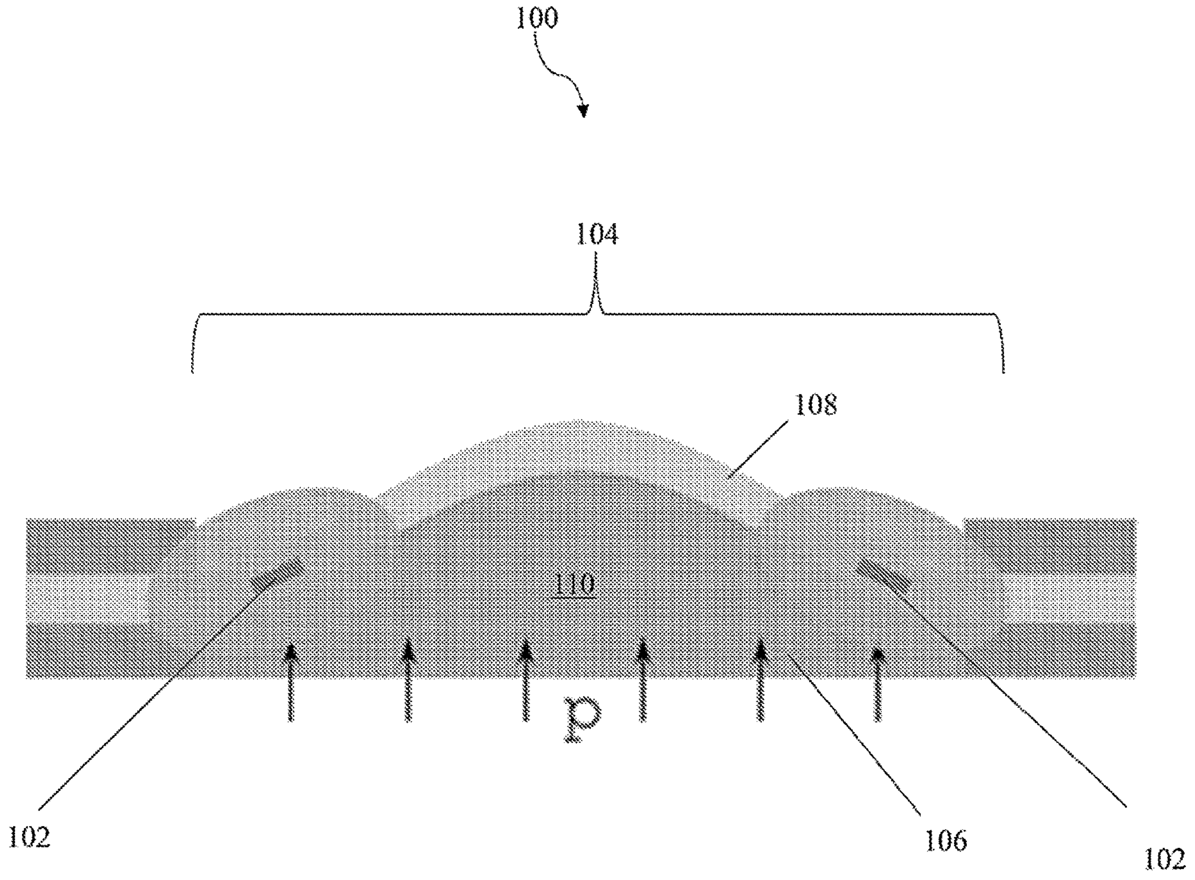
Fig. 1 (Prior Art)
FIG. 1 shows a cross-sectional side view of a heat-rupturable membrane of a device according to the prior art.

To treat a patient, a clinician may employ a material (e.g., a drug) consisting of large and complex molecules. In numerous instances, it may be desirable for the clinician to actively trigger the release of such material into a patient. For example, a device for delivering one or more drug payloads may benefit from active triggering. Generally speaking, active triggering may be used to initiate drug delivery, actuate hydraulic cylinders, or mix chemical reactants, among other suitable applications. For example, some prior systems actuate delivery of a fluid using an electrothermal valve including a polymer membrane to retain the fluid and a power source (e.g., a battery) for activating the electrothermal valve. The electrothermal valve is opened using the power source to actuate a heater configured to rapture (e.g., melt) the membrane. However, the Inventors have recognized that these devices including heat rupturable membranes suffer from several limitations. Specifically, devices including a heater directly embedded in, or disposed on, a portion of a membrane exposed to the payload and/or external environment surrounding the device may experience heat losses to the environment and/or the payload (e.g., a drug for delivery) during actuation. Moreover, in cases where a pressurized payload is used, the membrane and/or the heater may be exposed to large static pressures and deformations prior to and during actuation. This may result in the heater cracking or otherwise being damaged prior to actuation. For example, a resistive heater including a cracked heating trace may develop a hot spot leading to uncontrolled early rupturing of the membrane at a single spot rather than along a desired rupturing path.

In view of the above, the Inventors have recognized the advantages of a device having an active triggering mechanism with a heater isolated from both an environment surrounding the device and/or the payload contained within the device. For example, in some instances, a device may include a heater that is thermally coupled to a membrane of the device but is thermally insulated and/or physically removed from the deformable (e.g., rupturable) portion of the membrane of the device extending across an opening associated with an outlet of the device. Accordingly, the rupturable portion of the membrane may be exposed to both an external environment surrounding the device as well as the payload of the device while the heater is removed from, and in some instances thermally insulated from the payload and/or environment. This may also reduce the deformations applied to the heater during storage and operation of the device. For example, in some embodiments, a method of dispensing a material (e.g., a payload) from a device capable of active triggering may include heating a heat rupturable membrane separating a reservoir from the external environment of a device using a heater that is thermally insulated from an external environment of a device and/or a reservoir of the device. The heated membrane may subsequently rupture once heated to a predetermined temperature by the heater. The material may then be dispensed from the device, for example, from an outlet fluidly connected with the reservoir to the external environment surrounding the device.

In some embodiments, a device may include a housing. The housing may include a reservoir (e.g., for holding a material) and an outlet separated by a heat rupturable membrane either disposed between the reservoir and outlet, in the outlet, on a downstream end of the outlet, and/or at any location along a flow path extending between the reservoir and the external environment surrounding the device. The heat rupturable membrane may be configured to selectively rupture, for example when exposed to heat from a heater. For example, the heat rupturable membrane may be made from a material that either softens and/or decomposes above a threshold temperature. In one embodiment, the threshold temperature may be a melting temperature of a material. To that end, the heater may be thermally coupled to the membrane, while also being thermally insulated from the environment surrounding the device and/or the reservoir. In some instances, the heater is electrically coupled to a power source, such that the power source selectively actuates the heater by applying a current and/or voltage to operate the heater to heat the membrane. In some instances, the device may include a valve formed from the heater, the heat rupturable membrane and a frame constructed to support the heater and membrane. To thermally insulate the heater from the environment surrounding the device and/or the reservoir the heater may be disposed within the frame. In turn, the heater may be thermally coupled to the membrane. As elaborated on below, the heater may either be directly coupled to a portion of the membrane or indirectly to the membrane to apply heat to the membrane. Thus, the heater may heat the membrane to selectively rupture the membrane while being thermally insulated from the environment surrounding the device and/or the reservoir, within the frame. In some instances, a device may include one such valve, while in others, a device may include multiple such valves, depending on the application.

The heat rupturable membranes described herein may be may of any suitable material. For example, in some instances, the membrane may be made of a thermoplastic polymer such as parylene, polyethylene, or any other suitable polymer. Implementations incorporating non-polymer materials are also contemplated, as any appropriate heat rupturable material capable of being softened or decomposed at a desired threshold temperature may be employed. Alternatively or additionally, the heat rupturable membrane may be formed of a material that fractures upon heating. For example, semiconductive materials, ceramic materials, or glass materials may be employed. In some instances, the membrane may be formed from a metal. In instances where a metallic membrane, or a membrane including a metallic layer, is used, the metallic portion of the membrane may be electrically isolated from the heater. In some embodiments, the membrane includes multiple layers. Each layer of the membrane may be made of the same material, though in some applications, the layers may me made of different materials. Of course, the membrane may be made of any suitable material, depending on the application.

The heater may be made of any suitable material. For example, in some instances, the heater may be made of a conductive metal such as platinum, copper, gold, aluminum, nickel, titanium, tungsten, or any other suitable metal for performing Ohmic heating due to a current passing through the material.

While any appropriate type of heater may be used, in some instances, a heater may be a resistive heater corresponding to a resistive conductor, such as a resistive wire or trace. For example, the heater may be configured to produce heat when an electric current is passed through a resistive portion of the heater (e.g., Joule heating, Ohmic heating, etc.). This heat may then be transferred to a desired portion of the membrane to soften and/or decompose one or more portions of the membrane as elaborated on below. To that end a power source may selectively provide an electric current to the heater to heat the heater. The power source may supply either direct current or alternating current, depending on the application. The power source may be any suitable type of power source. For example, the power source may be a battery or a super capacitor. Of course, other suitable power sources may be employed, depending on the application. Additionally, other types of heaters may also be used.

The device may be configured to deliver any suitable material. For example, the material may be a gas, a viscous fluid, a non-viscous fluid, an aerosolized powder, and/or other appropriate type of material that is capable of being dispensed from a reservoir of a device through an outlet in fluid communication with an exterior of the device, as the present disclosure is not so limited. Accordingly, it should be understood that the materials described herein are not limited to any particular type of material.

A device according to the embodiments disclosed herein may be used in any suitable active triggering application. For example, in some instances, a device containing a material, such as an active pharmaceutical ingredient (API), may be actively triggered to deliver the material to a patient, for example at a particular location within the GI tract of the patient. Alternatively or additionally, the active triggering mechanism may be used in non-medical applications, including, for example, to move a hydraulic cylinder based on a pressure applied to the hydraulic cylinder from the material contained within the reservoir of the device; combine the material contained within the reservoir with a second material in a reaction chamber to initiate a chemical reaction; and/or any other appropriate application as the disclosure is not so limited.

As used herein, the term "active pharmaceutical ingredient" (also referred to as a "drug" or "therapeutic agent")

refers to an agent that is administered to a subject to treat a disease, disorder, or other clinically recognized condition, or for prophylactic purposes, and has a clinically significant effect on the body of the subject to treat, prevent, and/or diagnose the disease, disorder, or condition. The active pharmaceutical ingredient may be delivered to a subject in a quantity greater than a trace amount to affect a therapeutic response in the subject. In some embodiments, active pharmaceutical ingredients (APIs) can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals. Certain such APIs may include molecules such as proteins, peptides, hormones, nucleic acids, gene constructs, etc., for use in therapeutic, diagnostic, and/or enhancement areas. In certain embodiments, the API is a small molecule and/or a large molecule.

In some instances, the device may jet the material (e.g., an API) out of the device. For example, the device may be configured to eject the material from the device at a velocity sufficient for the material to penetrate a layer of tissue located adjacent to an outlet of the device (e.g., a GI tract mucosal lining in the context of an ingestible drug delivery device). To that end, the device may be equipped to apply a pressure to the material to achieve the desired velocity for a given application. In other instances, however, the material need not be jetted from the device as in some applications, the device may dispense the material at a lower velocity that would not penetrate tissue.

According to exemplary embodiments described herein, a trigger of a device may be configured to actuate the device in any appropriate manner. For example, in some instances, the device may be configured to actuate in response to a predetermined condition. In some embodiments, the predetermined condition may be the elapsing of a predetermined time. For example, in embodiments the device may be configured to deliver a drug payload after a predetermined time, such as a predetermined time after ingestion of the device. In other embodiments, a device may be configured to be actuated upon exposure to a particular environmental condition such as a predetermined condition at a predetermined location in the GI tract. This may include physical contact with the GI tract, physical manipulation in the GI tract (e.g., compression via peristalsis), one or more characteristics of the GI tract (e.g., pH, pressure, temperature, etc.), or combinations thereof. In some embodiments, the actuator may be a passive component. For example, in some embodiments the trigger may include a dissolvable material such as an enteric coating, sugar plug, and/or other dissolvable material, configured to dissolve in the GI tract. The dissolvable material may have a certain thickness and/or shape that at least partly determines the speed at which the material dissolves and ultimately actuates the device. In one such embodiment, the material may dissolve to expose a sensor or electrodes use to trigger actuation of a heater of the device. Appropriate materials for a dissolvable trigger may include, but are not limited to, sugar alcohols, such as disaccharides (e.g. Isomalt), water soluble polymers, such as Poly-vinyl alcohol, enteric coatings, time-dependent coatings, enteric and time-dependent coatings, pH responsive coatings, temperature-dependent coatings, light-dependent coatings, and/or any other appropriate material capable of being dissolved within the GI tract of a subject or other appropriate environment. In other embodiments, a device may include a sensor that detects one or more characteristics prior to actuation. For example, in some embodiments, a sensor detecting contact with a GI mucosal lining may be used to actuate the device. Other types of actuators may include an electrical timer, a light sensor, an enzymatic sensor, a conductivity sensor, a pH sensor, a pressure sensor, a temperature sensor, and/or any other appropriate sensor or construction capable of providing a signal to a processor or closing an electrical circuit associated with a processor or other portion of the device when that the device is exposed to one or more predetermined conditions corresponding to a desired target location within the GI tract, other anatomical structure, or other appropriate environment. Accordingly, it should be understood that the devices disclosed herein are not limited to the use of any specific type of trigger.

In some embodiments, as described above, a device may include a processor that selectively actuates the device. Specifically, the processor may be capable of selectively providing power from a power source to a heater (e.g., as described above) to heat the membrane. Thus, the processor may selectively rupture the membrane by selectively actuating the heater. Depending on the specific type of membrane used in the device, the processor may selectively operate the heater of the device in any suitable manner. Of course, it should be understood that embodiments not including a processor are also contemplated. For example, in some embodiments, two electrodes may be placed into electrical communication with one another when exposed to an electrically conductive liquid to close an electrical circuit including a heater to actuate the device without the need for a processor. Thus, the current disclosure should not be limited to embodiments only including processors as the disclosure is not so limited.

In some embodiments, a device may include a potential energy source for pressurizing a material disposed in a reservoir of the device to dispense the material from the reservoir through an associated outlet. In some embodiments, the potential energy source may be a compressed gas. The compressed gas may be directly stored in the device, or the compressed gas may be generated via a chemical reaction or phase change. For example, in some embodiments dry ice may be stored in a chamber of the device so that compressed gas is generated as the dry ice sublimates. Alternatively, a compressed gas may be provided to a desired chamber prior to sealing a device. In some embodiments, the potential energy source may be a spring (e.g., a compressed compression spring). In some embodiments, the potential energy source may be a reaction chamber. For example, the reaction chamber may allow an acid and base to be combined to generate gas, leading to the expulsion of material when the delivery device is actuated. Alternatively, in another embodiment, the potential energy source may be an explosive material located within a chamber to generate pressurized gas for expelling the material from the device. Of course, any suitable reaction or other potential energy source may be employed to pressurize and drive a material out of a reservoir of the device when the device is actuated, as the present disclosure is not so limited.

Depending on the embodiment, a processor may also be configured to actuate a potential energy source of a device. For example, in some embodiments, the processor may provide an electrical current to the potential energy source to activate it, when appropriate. Of course, the processor need not actuate the potential energy source as the potential energy source may be activated separately from the processor by a separate trigger and/or the potential energy source may be pre-energized such that the reservoir is already pressurized prior to opening of the one or more valves of a device (e.g. a preloaded spring, compressed gas, or other construction). For example, the potential energy source may be actuated by a mechanical process, a chemical process, or other suitable process. Alternatively, a separate trigger, including any of those described herein, may be used for actuating the potential energy source as the disclosure is not limited to how a potential energy source applies a driving force to expel a material from a reservoir of a device. Additionally, in such embodiments, triggering of the potential energy source may occur either prior to, at the same time, or after actuation of a trigger to rupture a membrane of the device.

As noted previously, in some embodiments, a device as described herein may be configured to deliver a predetermined payload of a material to a subject. In such an embodiment, a device may include a reservoir volume less than or equal to 500 μL, 300 μL, 200 μL, 150 μL, 100 μL, 75 μL, 50 μL, 25 μL, 10 μL, and/or any other appropriate volume. Correspondingly, a device may contain a reservoir volume greater than or equal to 1 μL, 5 μL, 10 μL, 25 μL, 50 μL, 75 μL, 100 μL, 200 μL, 300 μL, and/or any other appropriate volume. Combinations of the above-noted volumes are contemplated, including, but not limited to, reservoir volumes between 1 μL and 500 μL, between 1 μL and 300 μL, between 1 μL and 200 μL, between 1 μL and 150 μL, between 1 μL and 100 μL, between 1 μL and 75 μL, between 1 μL and 50 μL, between 1 μL and 25 μL, between 1 μL and 10 μL, between 10 μL and 500 μL, between 10 μL and 300 μL, between 10 μL and 200 μL, between 10 μL and 150 μL, between 10 μL and 100 μL, between 10 μL and 75 μL, 10 μL and 50 μL, between 10 μL and 25 μL, between 25 μL and 500 μL, between 25 μL and 300 μL, between 25 μL and 200 μL, between 25 μL and 150 μL, between 25 μL and 100 μL, between 25 μL and 75 μL, between 25 μL and 50 μL, between 50 μL and 500 μL, between 50 μL and 300 μL, between 50 μL and 200 μL, between 50 μL and 150 μL, between 50 μL and 100 μL, between 50 μL and 75 μL, between 75 μL and 500 μL, between 75 μL and 300 μL, between 75 μL and 200 μL, between 75 μL and 150 μL, between 75 μL and 100 μL, between 100 μL and 500 μL, between 100 μL and 300 μL, between 100 μL and 200 μL, between 100 μL and 150 μL, between 150 μL and 500 μL, between 150 μL and 300 μL, between 150 μL and 200 μL, between 200 μL and 500 μL, between 200 μL and 300 μL, or between 300 μL and 500 μL. Of course, any suitable reservoir volume may be employed in a device, as the present disclosure is not so limited.

Though other applications are contemplated, in some embodiments, a device is sized and shaped to be ingested by a subject (e.g., a patient). Accordingly, the device may be appropriately small so that the device may be easily swallowed and subsequently pass through the GI tract, including the esophagus and pyloric opening within the stomach. In some embodiments, a device may include an overall length, such as a maximum dimension along a longitudinal axis of the device, that is less than or equal to 40 mm, 30 mm, 20 mm, 10 mm, 5 mm, and/or another appropriate length. Correspondingly, a device may have an overall length greater than or equal to 3 mm, 5 mm, 10 mm, 20 mm, 25 mm, and/or another appropriate length. Combinations of the above-noted ranges are contemplated, including, but not limited to, overall lengths between 5 mm and 30 mm, between 10 mm and 30 mm, between 20 mm and 30 mm, between 25 mm and 30 mm, between 5 mm and 25 mm, between 10 mm and 25 mm, between 20 mm and 25 mm, between 5 mm and 20 mm, between 10 mm. In some embodiments, a device may have a maximum external transverse dimension, such as a diameter or other dimension that may be perpendicular to the longitudinal axis, that is less than or equal to 11 mm, 10 mm, 7 mm, 5 mm, and/or another appropriate dimension. Correspondingly, a device may have a maximum external transverse dimension greater than or equal to 3 mm, 5 mm, 7 mm, 9 mm, and/or another appropriate dimension. Combinations of the above-noted ranges are contemplated, including, but not limited to, maximum external transverse dimensions between 3 mm and 11 mm, between 3 mm and 10 mm, between 3 mm and 7 mm, between 3 mm and 5 mm, between 5 mm and 11 mm. In some embodiments, a device may have an overall volume less than or equal to 3500 $mm^3$, 3000 $mm^3$, 2500 $mm^3$, 2000 $mm^3$, 1500 $mm^3$, 1000 $mm^3$, 750 $mm^3$, 500 $mm^3$, 250 $mm^3$, 100 $mm^3$, and/or any other appropriate volume. Correspondingly, a device may have an overall volume greater than or equal to 50 $mm^3$, 100 $mm^3$, 250 $mm^3$, 500 $mm^3$, 750 $mm^3$, 1000 $mm^3$, 1500 $mm^3$, 2000 $mm^3$, 2500 $mm^3$, and/or any other appropriate volume. Combinations of the above-noted ranged are contemplated, including, but not limited to, volumes between 1000 $mm^3$ and 3000 $mm^3$, 1500 $mm^3$ and 3000 $mm^3$, 50 $mm^3$ and 500 $mm^3$, 50 $mm^3$ and 100 $mm^3$, as well as 2000 $mm^3$ and 3000 $mm^3$. Of course, any suitable overall length, maximum external transverse dimension, and volume for a device may be employed, as the present disclosure is not so limited.

According to exemplary embodiments described herein, the device may be used in medical applications. For example, in some instances, the device may be administered to a subject orally. In other embodiments, the device may be administered, rectally, vaginally, or nasally as the present disclosure is not so limited. Additionally, in some cases a device according to exemplary embodiments described herein may be implanted into an organ of a subject. For example, a device may be implanted into the arm, brain, peritoneum, etc. of the subject.

Though medical applications are primarily discussed herein, it should be appreciated that active triggering of the disclosed heat rupturable membranes may have applicability in numerous other fields, as the present disclosure is not so limited. For example, as described above, the device may be configured to actuate a hydraulic cylinder in any suitable manner or application (e.g., an industrial application). Further, the device may be capable of actuating a chemical reaction in any suitable manner or application (e.g., an explosive application). Thus, the device may be employed in any suitable application.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 shows a conventional design of a device 100 including a heat rupturable membrane 108 for selectively containing a material 110 disposed within a reservoir 106 of the device 100. The heat rupturable membrane 108 may serve to separate the material 110 from an outlet 104 of the device 100 such that the material 110 is retained within the reservoir 106. The heat rupturable membrane 108 may be configured to be selectively rupturable by a heater 102 disposed on or in a portion of the membrane 108 exposed to the pressurized material contained in the reservoir and/or the exterior environment. Particularly, the heater 102 may be thermally coupled to the membrane 108 such that when heater 102 is actuated, membrane 108 may rupture, opening fluid communication between the material 110 contained within the reservoir 106 and the outlet 104, allowing the material 110 to be ejected from the device 100. Thus, during operation, the heater 102 may transfer heat to both the membrane as well as the surrounding liquids (e.g., the material 110 or surrounding environment). Accordingly, the material in the reservoir as well as the environment may act as a parasitic heat sink, preventing a portion of the heat from being transferred to the membrane 108. This may increase a power needed to reliably rupture the membrane and/or may potentially prevent the membrane 108 from rupturing as intended.

Figure 2:
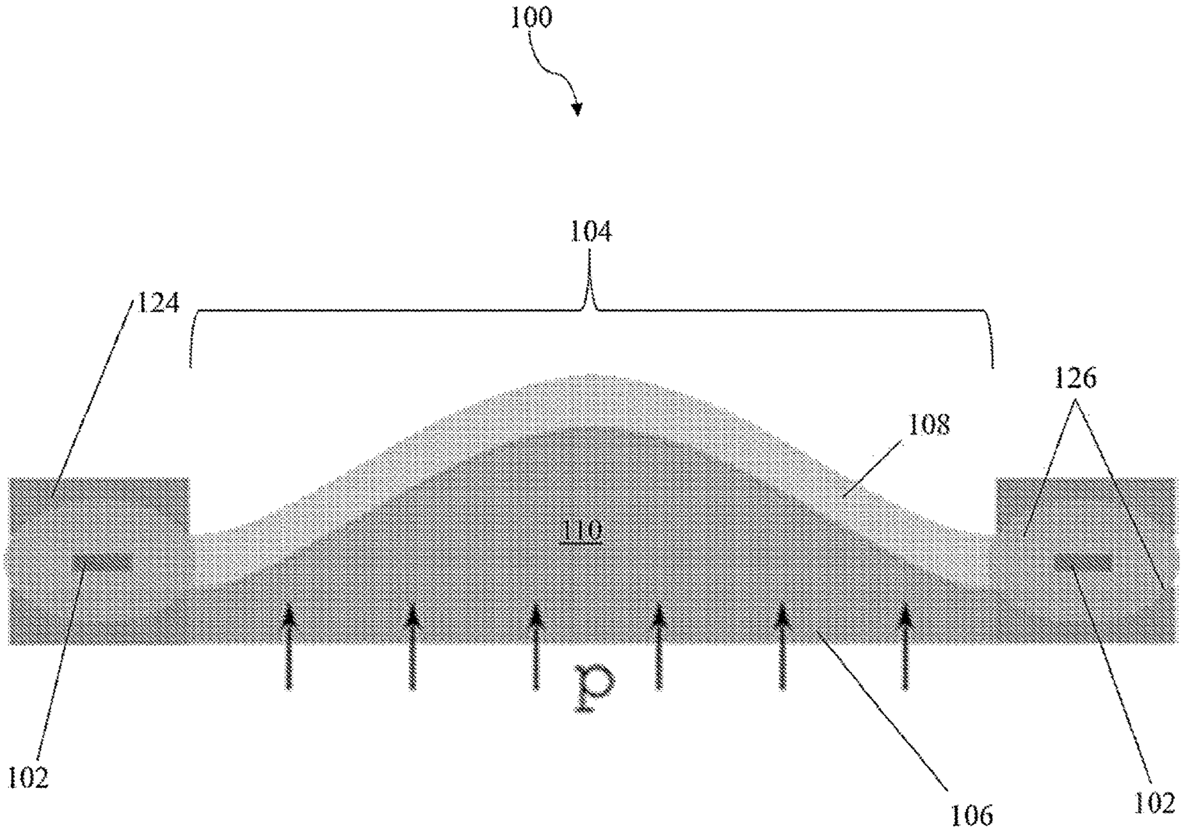
FIG. 2 shows a cross-sectional side view of a heat rupturable membrane of a device according to one illustrative embodiment.

In addition to the above, in some applications, the material 110 within the reservoir 106 may be pressurized either prior to and/or during actuation which may apply a static pressure p to the membrane 108. For example, in some instances, the material 110 may be pressurized within the reservoir 106 such that the material 110 is expelled from the reservoir 106 when membrane 108 ruptures. However, the static pressure p may serve to deflect the membrane 108 which will apply tensile stresses to the various portions of the membrane 108 and the resistive heating traces of the heater 102 (e.g. a conductive trace or wire) disposed on or in the membrane. These stresses and resulting deformations may contribute to the premature cracking or tearing of the heater 102, which may adversely affect the ability of heater 102 to produce a desired amount and/or distribution of heat, which may potentially prevent the heater 102 from rupturing the membrane 108 when the heater 102 is actuated. For example, in some instances, when the heater trace is cracked, there may be less area available to accept a current to heat the membrane 108 which will increase the local resistance of the heater leading to a hot spot with an increased temperature relative to the rest of the heater. This may result in uncontrolled rupturing of the membrane at an unintended portion of the membrane and/or on only a fraction of the intended portion of the membrane. Additionally, in extreme cases, the conductive path formed from the heater traces may be completely severed by the fracture preventing any operation of the device. In view of the above, the Inventors have recognized the advantages associated with a configuration where the heater 102 is removed from a portion of a heat rupturable membrane 108 that is exposed to the exterior environment and/or material contained within the device, see FIG. 2. Particularly, in some embodiments, a device may include a frame 124 which may either be a separate component or an integral part of a housing of the device. In the depicted embodiment, a first portion of the membrane and the heating traces of the heater 102 are disposed between opposing portions of the frame 124, i.e. between opposing surfaces 126. Depending on the embodiment, the conductive paths corresponding to the heating traces of the heater may be disposed in or on the membrane as the disclosure is not so limited. Embodiments in which a heater is not in direct contact with a portion of the membrane are also contemplated. In either case, the first portion of the membrane and heater may be held in place either by a clamping force applied between the opposing portions of the frame, the use of an adhesive, and/or any other appropriate attachment method. The frame may include an opening corresponding to an outlet 104 of the device. A second portion of the membrane may extend across this opening such that the membrane seals the reservoir and/or outlet relative to an exterior environment surrounding the device. Since the depicted heater 102 is held within the frame 124 of the device 100, and outside of the area of the membrane 108 pressurized by the pressure p, the heater 102 may be thermally insulated from the material contained in the reservoir and the surrounding environment while still being thermally coupled with the adjacent portions of the membrane contained within and adjacent to the opening of the frame. This may reduce parasitic losses from the heater during actuation of the valve due to the heater being more insulated relative to the reservoir and external environment compared to embodiments where the heater is integrated into a portion of the membrane contained in the opening of the outlet.

In some instances, it may be desirable to increase a thermal isolation of a heater relative to the reservoir 106 and/or external environment surrounding a device. In such an embodiment, a frame 124, or other structure, which a membrane 108 or heater is associated with may be made from a thermally insulating material. For example, the frame or other component of a device may be made from polytetrafluoroethylene which may exhibit a low thermal conductivity as well as a high glass transition temperature, allowing the surfaces 126 to be in contact with the heater 102 with reduced degradation or without degradation. In therapeutic delivery applications, the materials may also be selected to be biocompatible. Of course, the frame 124 or other portions of a device need not be formed of polytetrafluoroethylene as any suitable material may be used depending on the application.

Figure 3:
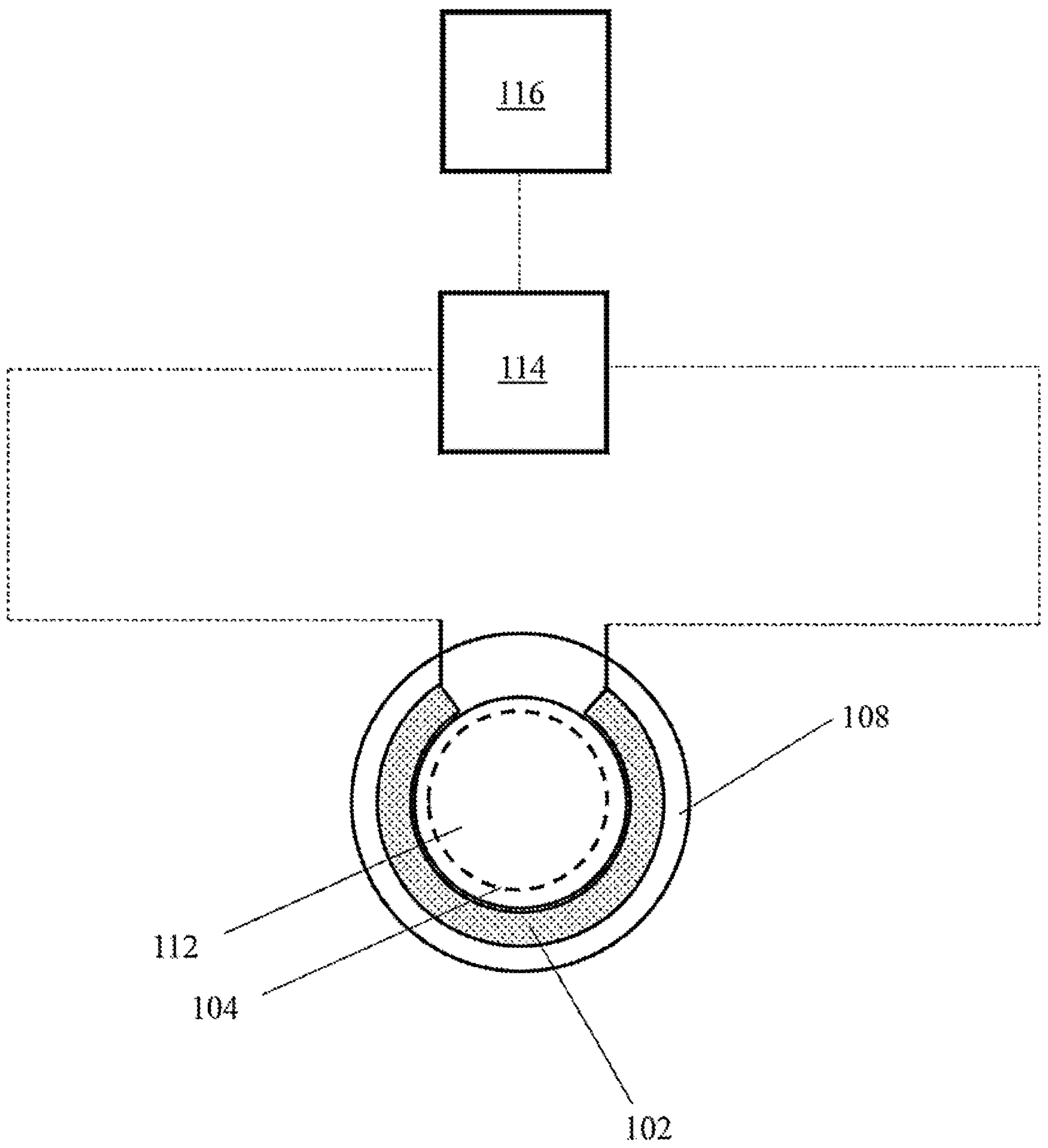
FIG. 3 is a top view of a heat rupturable membrane of a device according to one illustrative embodiment.

As described above, in some embodiments, a heater 102 of a device may be a resistive heater including one or more conductive pathways in the form of wires, traces, or other structure capable of conducting a current to generate heat via Ohmic heating. FIG. 3 depicts one such arrangement of a conductive pathway of a heater relative to a heat rupturable membrane. In the depicted embodiment, the heater 102 may be shaped with a particular geometry to rupture the membrane 108 in a specific shape such that the membrane 108 may rupture in a defined and suitable manner to provide a uniform and reproducible opening of the disclosed valve. For example, in the embodiment depicted in FIG. 3, the heater 102 is configured such that the heater 102 extends partially around an opening corresponding to an outlet 104 of the device, see dashed circle corresponding to the opening on the opposing side of the membrane, with a gap present between an upstream and downstream portion of the heater relative to the power source. In the depicted embodiment, the heater forms a C, U, or horseshoe shaped path extending partially around the opening. However, any appropriate geometry for the path of the heater around the opening may be used as the disclosure is not so limited. Additionally, while a single heater is depicted, multiple heaters may be used as well. In either case, during operation, the heater may heat the thermally coupled portions of the membrane such that they are heated to a temperature equal to or greater than a softening, decomposition, melting, or other appropriate temperature of the membrane. This may result in the membrane rupturing along a length of the heater 102, creating a flap 112. The flap 112 may serve to create a defined opening in the membrane 108, allowing the material contained in the device to be expelled out from the reservoir through the flap. The creation of flap 112 may further serve to reduce the risk of the membrane 108 rupturing in a meandering or undefined manner, potentially inhibiting the ejection of the material from the reservoir. Of course, while the use of a flap where a heater only extends partially around an opening is described, the use of heaters that apply heat to a membrane along an entire perimeter of an associated opening are also contemplated as the disclosure is not limited in this fashion.

During operation, the heater 102 may be electrically connected to a power source 114, which may selectively provide a current to the heater 102 to generate heat. Depending on the application, the power source 114 may be a small portable power source such as a battery or a supercapacitor. However, in certain applications, including larger non-medical applications, the power source 114 may not be portable, taking the form of a power supply unit, power generator, a power cord connected with a local power grid, or other suitable power source. Thus, the power source 114 may be any suitable type of power source, depending on the application. Regardless of the specific power source, the power source may be operatively coupled to a processor 116. Accordingly, the processor 116 may be capable of selectively activating the power source 114 to provide current to the heater 102 to pass a current through the conductive material of the heater 102 to generate heat therein to resistively heat the rupturable membrane 108. Though it should be noted that other types of heaters may be used to heat the membrane. In turn, the power source 114 may provide electrical power to the processor 116, though this need not be the case, as in some embodiments, the processor 116 may include an independent power source.

Additionally, it should be noted that in some embodiments, the device 100 need not include a processor at all, as other triggers may also be used as previously described.

Figure 4:
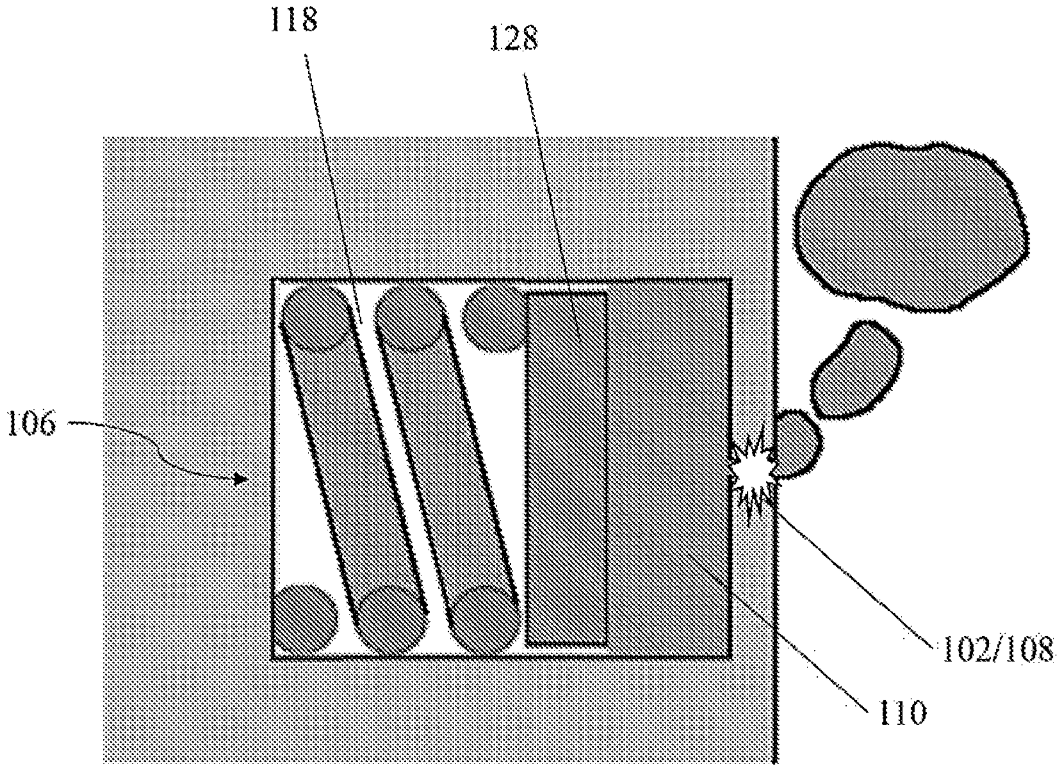
FIG. 4 shows a cross-sectional side view of a drug release chamber of an ingestible device including a heat rupturable membrane according to one illustrative embodiment.
Figure 5:
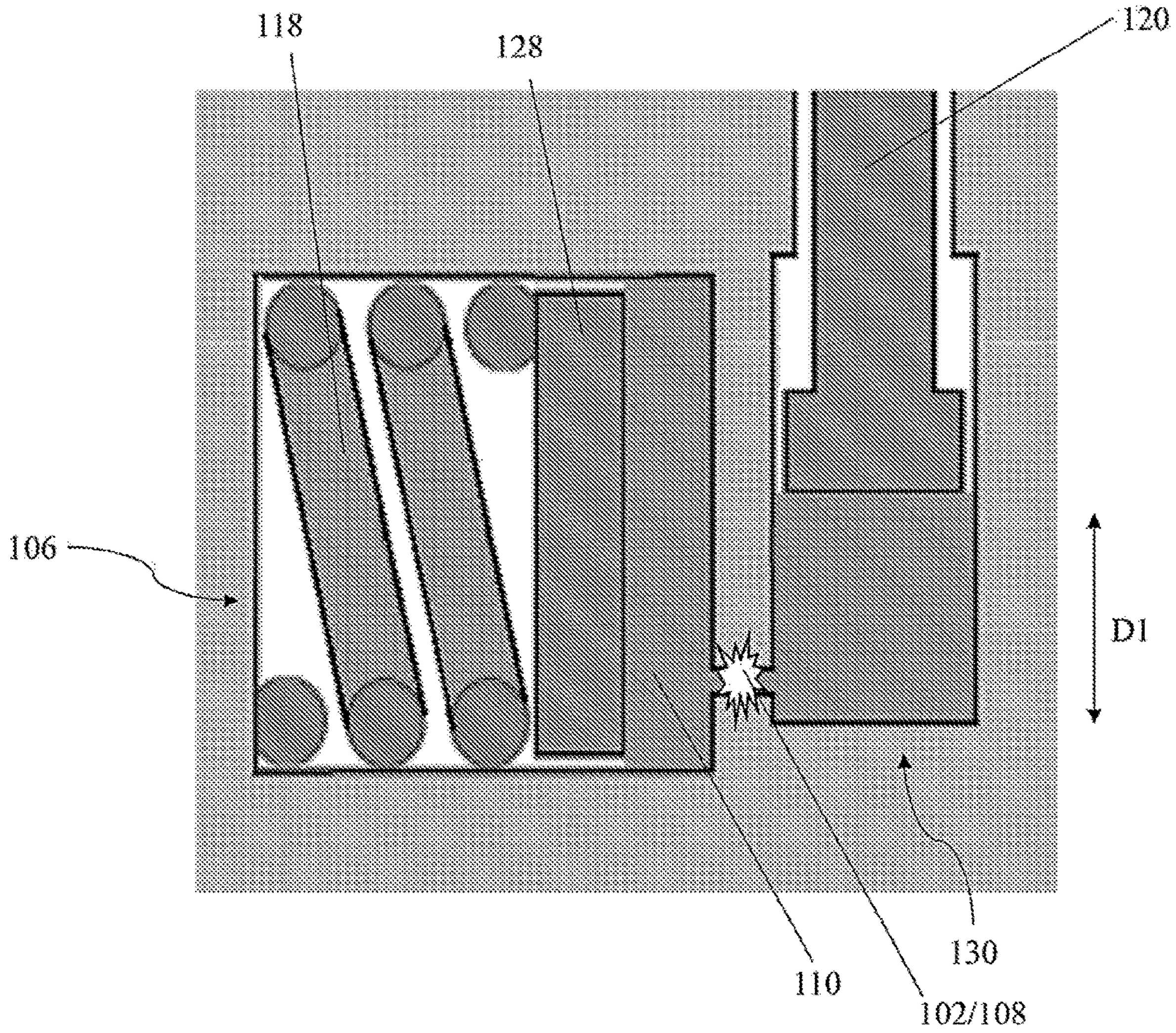
FIG. 5 shows a cross-sectional side view of a hydraulic cylinder actuator of a device including a heat rupturable membrane according to one illustrative embodiment.

In some instances, the material 110 may be ejected from the reservoir 106 for a number of suitable purposes. For example, FIG. 4 depicts an embodiment of a device 100 in a drug release application (e.g., for delivering an API to the GI tract of a patient). In the depicted embodiment, the device 100 is an ingestible device and the material 110 is an API. The API is configured to be dispensed (e.g., jetted) out of the reservoir 106 via a potential energy source 118. For example, the potential energy source 118 may be configured to apply a driving force to a piston 128 either prior to, during, and/or after opening of the membrane 108 using the heater 102 to drive the piston into the reservoir volume to pressurize the API contained therein. In some embodiments, this pressurized API may rupture a softened membrane 108, while in other embodiments the membrane 108 may be ruptured prior to the API being pressurized. In either case, once the membrane 108 is open and the reservoir 106 is pressurized, the API may be expelled from reservoir 106 out of the outlet 104. As noted previously, the potential energy source 118 may drive the piston 128 through the use of a compressed gas, a pre-loaded spring, a chemical reaction, the sublimation of dry ice, or any other suitable method. Of course, while the use of a piston driven system is illustrated in the figures, it should be understood that any appropriate method and/or system capable of applying a driving force to an API contained in a reservoir may be used as the disclosure is not so limited. In another embodiment, the potential energy source may alternatively be used to drive a hydraulic cylinder 120 as shown in FIG. 5. Particularly, after the membrane 108 is ruptured by the heater 102, the potential energy source may drive the piston 128 as described above to eject the material 110 (which in the depicted embodiment may be any suitable liquid) from the reservoir 106. The material may then in turn displace the hydraulic cylinder 120, forcing the hydraulic cylinder to move a prescribed distance. The prescribed distance may be based on the volume of the material 110 initially contained within the reservoir 106 and the volume of an extension chamber 130 configured to initially contain the hydraulic cylinder 120. Specifically, depending on the shape and size of the extension chamber 130 and the volume of the material 110 stored in the reservoir 106, the material 110 may displace the hydraulic cylinder by a predetermined distance D1.

Figure 6:
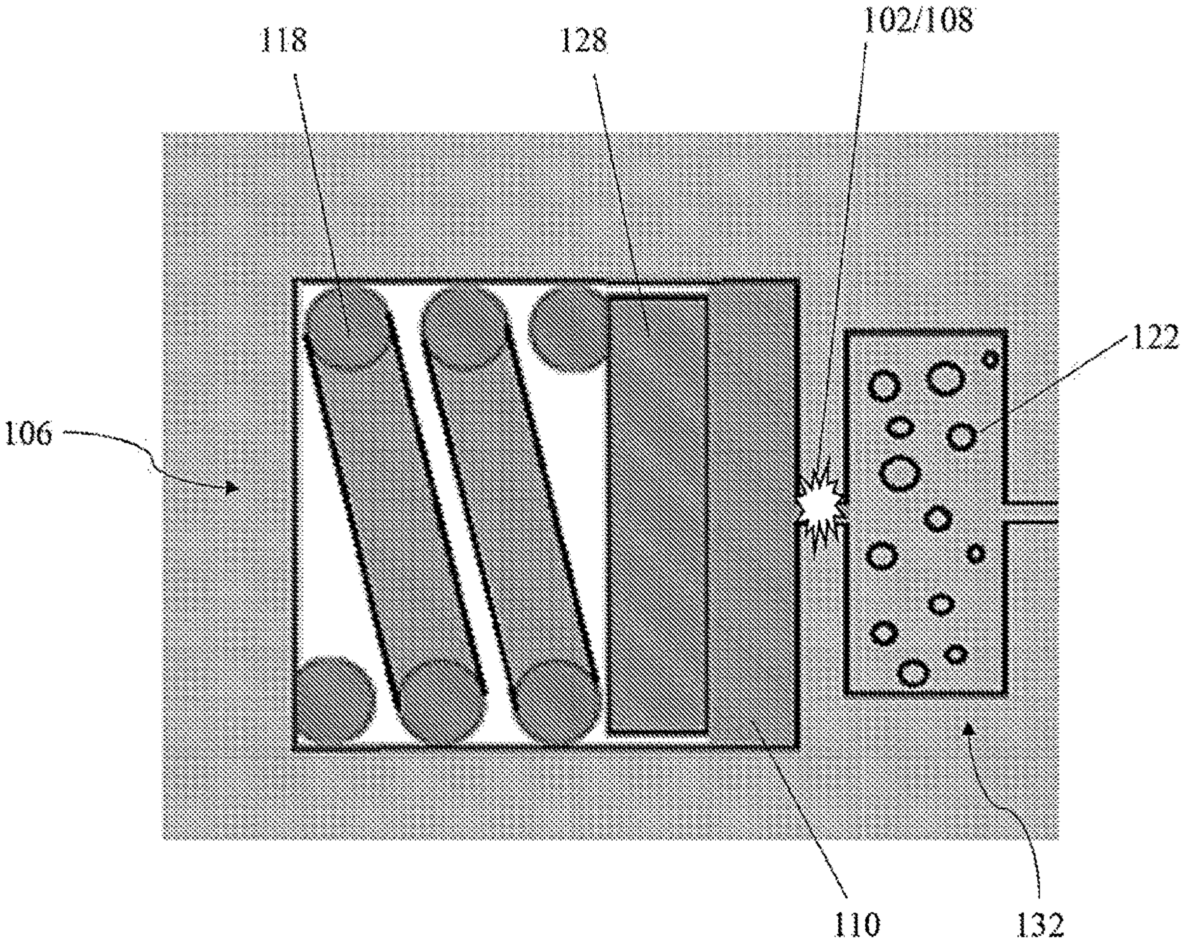
FIG. 6 shows a cross-sectional side view of a chemical mixing chamber of a device including a heat rupturable membrane according to one illustrative embodiment.

In yet another embodiment, the potential energy source may be used to combine two chemicals in a chemical mixing chamber 132, as depicted in FIG. 6. In the FIG. 6 embodiment, the potential energy source 118 drives the piston 128 to eject the material 110 from the reservoir 106 into the chemical mixing chamber 132, after the membrane 108 is ruptured by a heater 102. In the chemical mixing chamber 132, the material 110 may come into contact with a second material 122 complementary to the first material 110, such that the combination of the first material 110 and the second material 122 initiates a chemical reaction. Particularly, the first material 110 and the second material 122 are initially separated and chemically isolated from one another by the membrane 108. However, once the membrane 108 is ruptured and the potential energy source 118 is triggered, the first material 110 is free to mix with the second material 122, initiating a chemical reaction between the first and second materials 110, 122.

Figure 7:
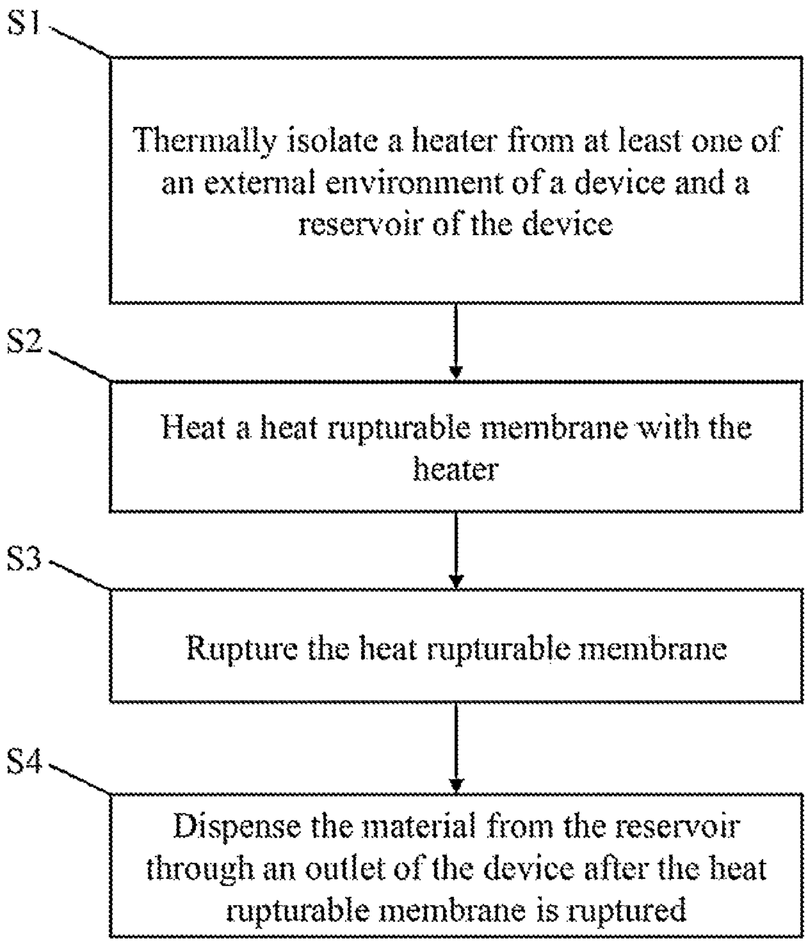
FIG. 7 is a flow chart of a method of dispensing a material from a device including a heat rupturable membrane according to one illustrative embodiment.

The present disclosure may also be embodied as a method of dispensing a material, as depicted in the flow chart of FIG. 7. At step S1, the heater 102 may be thermally insulated from at least one of an external environment of the device 102 and/or the reservoir 106. For example, as described above, the heater 102 may be disposed within the frame 124 of the device 100, while remaining thermally coupled to the membrane 108. Subsequently, at step S2, the heater 102 may be actuated, for example by the power source 114 and/or the processor 116 as described above to heat the membrane 108, which may serve to soften and/or decompose the membrane 108. Then at step S3, the membrane 108 may be ruptured, for example, exclusively due to the heat from the heater 102, due to a combination of the heat from the heater 102 and the potential energy source 118 of the reservoir 106, or in any other suitable manner. Thus, fluid communication between the reservoir 106 and the outlet 104 may be established. This allows the material 110 initially contained within the reservoir 106 to be dispensed from the reservoir 106 and flow out from the device 100 via the outlet 104.

Example: Thermal Finite Element Analysis of Model Device

Figure 8:
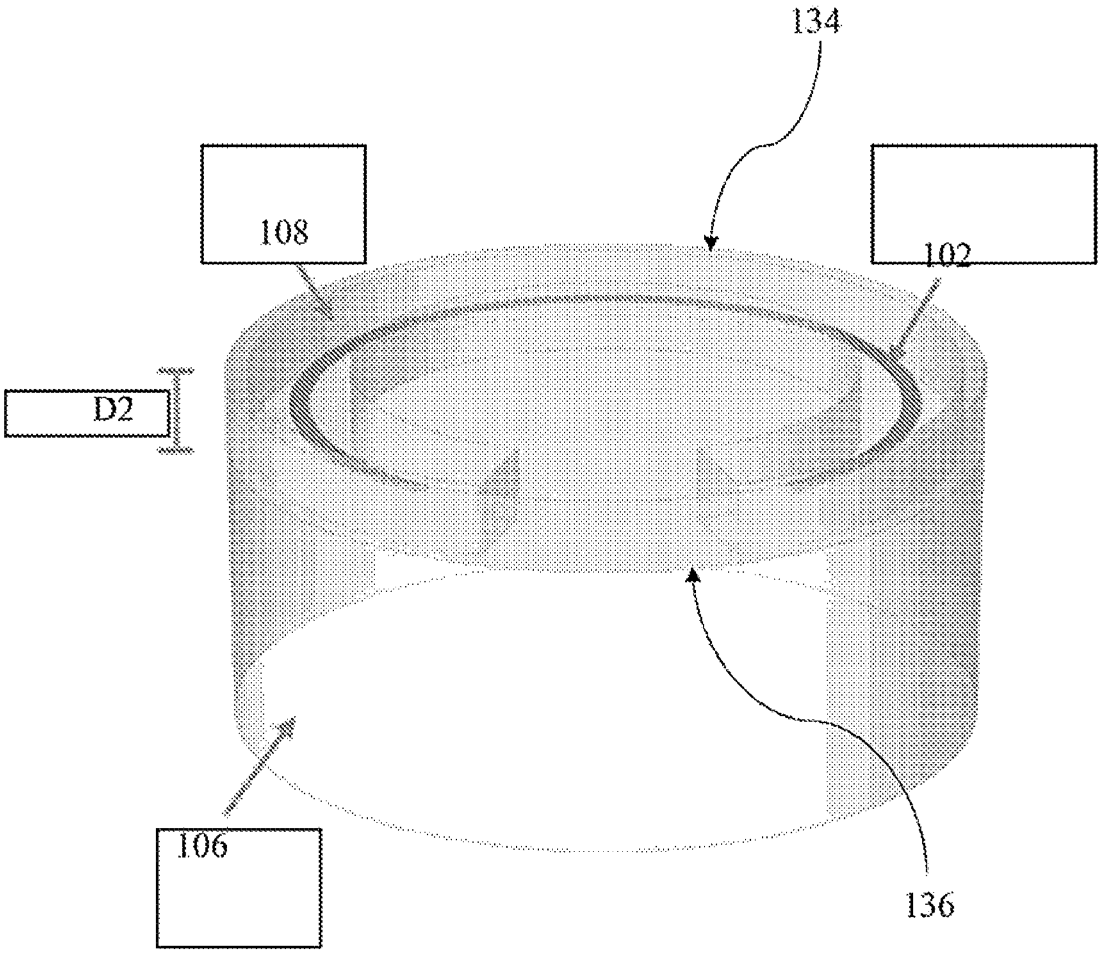
FIG. 8 is a perspective view showing the geometry of a valve of a device according to one illustrative embodiment.

To analyze and test an embodiment of a device 100 according to the present disclosure, the Inventors developed a time-dependent thermal Finite Element Model of the device 100 in COMSOL, shown in FIG. 8. In the model, the membrane 108 is formed from parylene. The model further utilizes an operating voltage 3.6V and a maximum current rating 32 mA provided by a Varta CP 7840 A3 lithium-ion battery. The model also considers changes in conductor resistivity due to heating as described by Equation (1) below:

$$\Delta R = \alpha R_0 \Delta T \tag{1}$$

Figure 9:
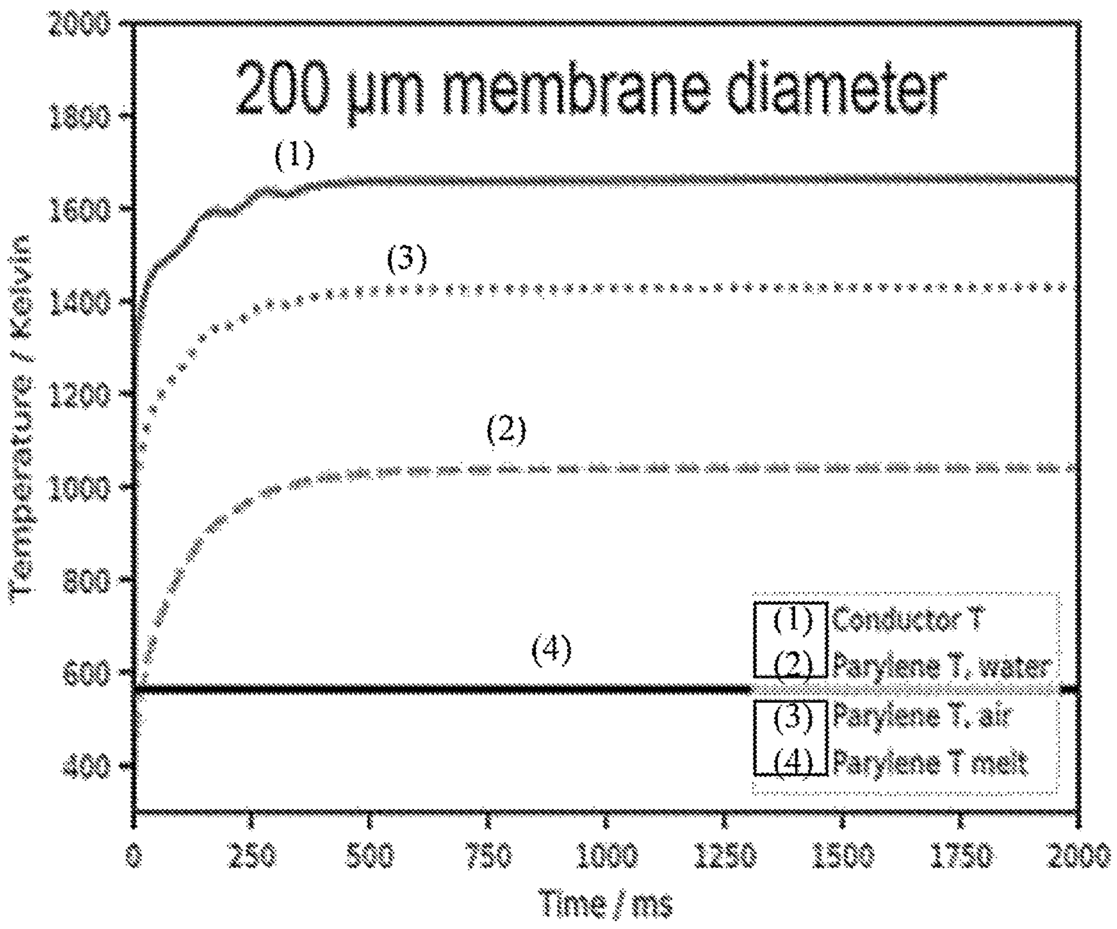
FIGS. 9-11 are charts showing time dependent thermal contours of a series of heat rupturable membranes according to a series of illustrative embodiments.
Figure 10:
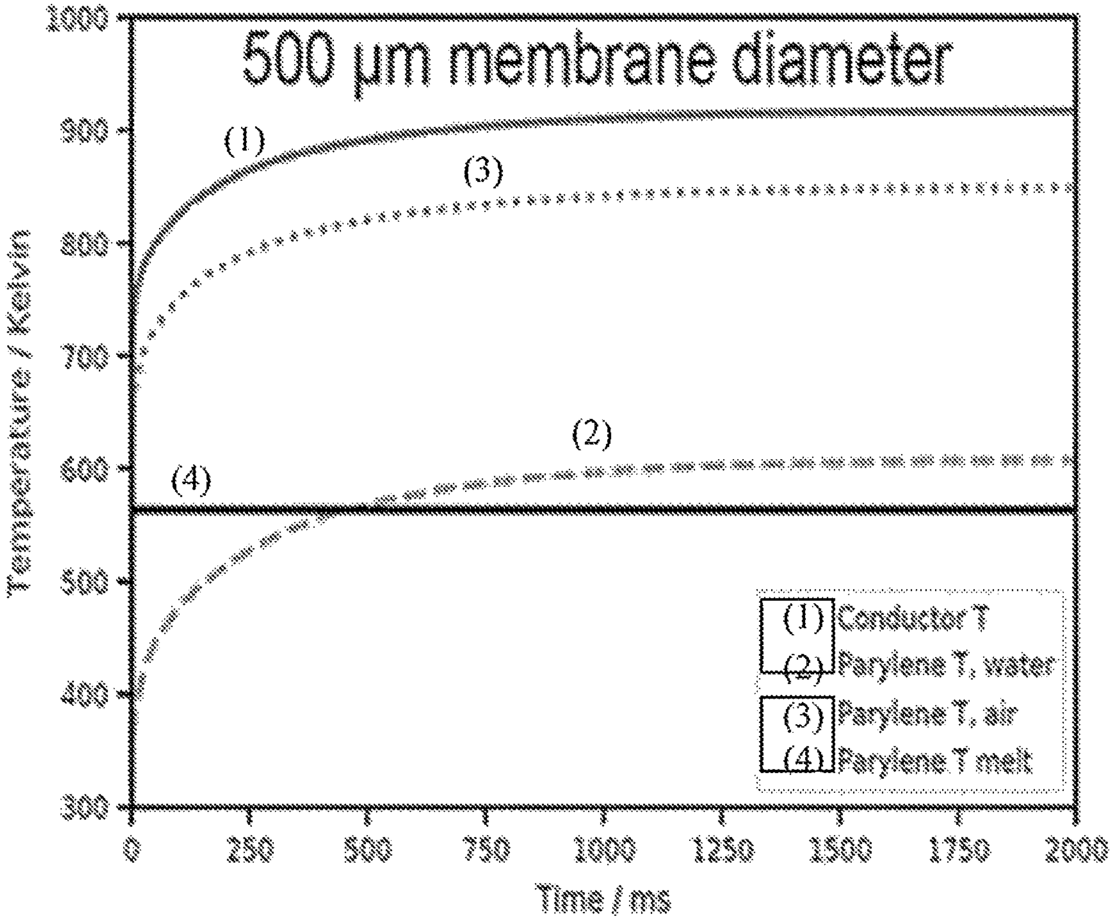
Figure 11:
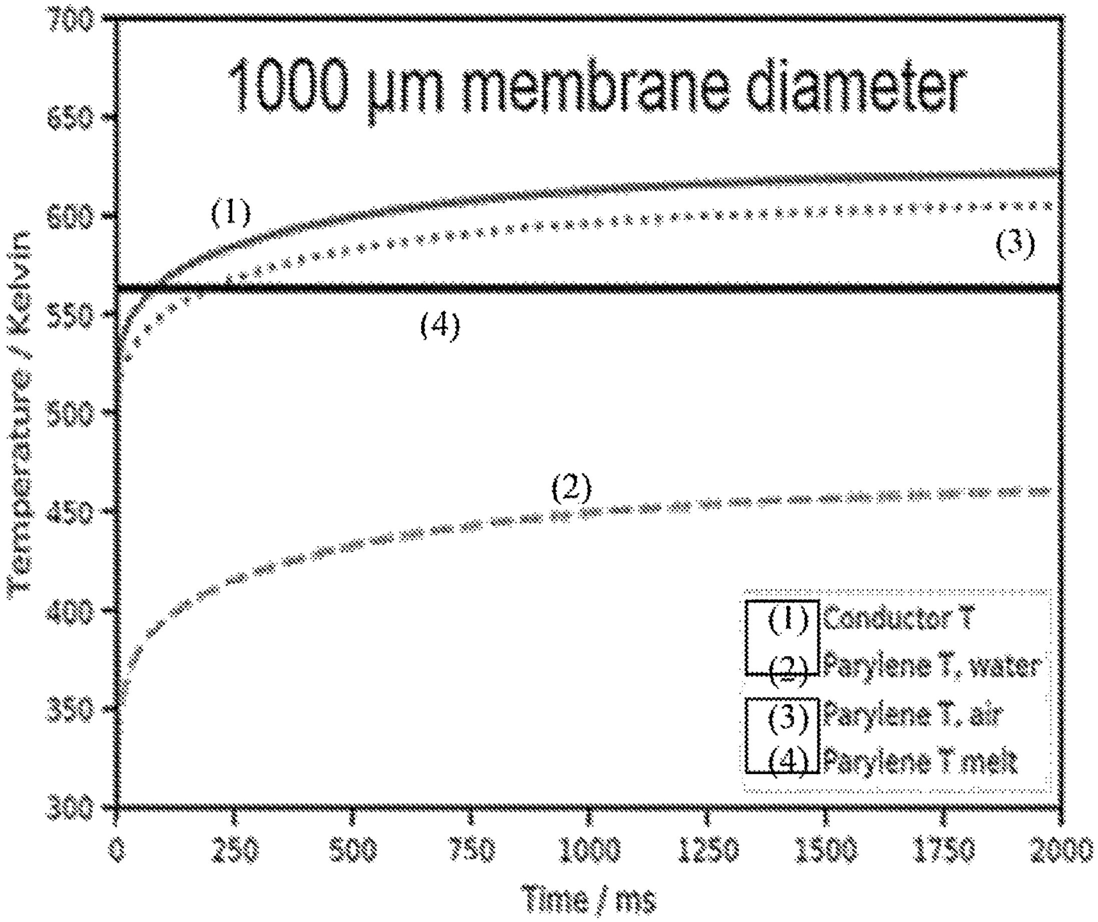

In the model, the heater 102 is formed from platinum, and it sits in the center of a layer of membrane 108 having a thickness D2. For purposes of this model, the thickness D2 is 20 μm. Beneath the membrane 108 is reservoir 106, which contains a column of water to simulate liquid drug, while a convective boundary with air is above the membrane 108, as shown in FIG. 8. FIGS. 9-11 illustrate a time-dependent temperature plot at varying locations along the membrane 108 of the model device. Particularly, line (1) in FIGS. 9-11 shows the time-dependent temperature of the heater 102 (e.g., a conductor) for membranes 108 having a 200 μm diameter, a 500 μm diameter, and a 1000 μm diameter respectively. Line (2) in FIGS. 9-11 shows the time-dependent temperature of the membrane 108 on the side in contact with the water (e.g., position 136 in FIG. 8) located in reservoir 106 for membranes 108 having a 200 μm diameter, a 500 μm diameter, and a 1000 μm diameter respectively. Line (3) in FIGS. 9-11 shows the time-dependent temperature of the membrane 108 on the side in contact with the air surrounding the model device (e.g., position 134 in FIG. 8) for membranes 108 having a 200 μm diameter, a 500 μm diameter, and a 1000 μm diameter respectively. Line (4) in FIGS. 9-11 shows the melting temperature of the material of membrane 108, which in each case was parylene. The data points were collected by using probes at each of the prescribed locations over the duration of the test.

The Inventors further developed an analytic model of the rupture strength of membrane 108. Thus, the inventors derived Equation (2) below from the theory of stress experienced in thin, circular membranes:

$$P_{break} = \sqrt{\frac{h^2\left(\frac{\sigma_{yield}}{0.423}\right)^3}{Ed^2}} \tag{2}$$

Figure 12:
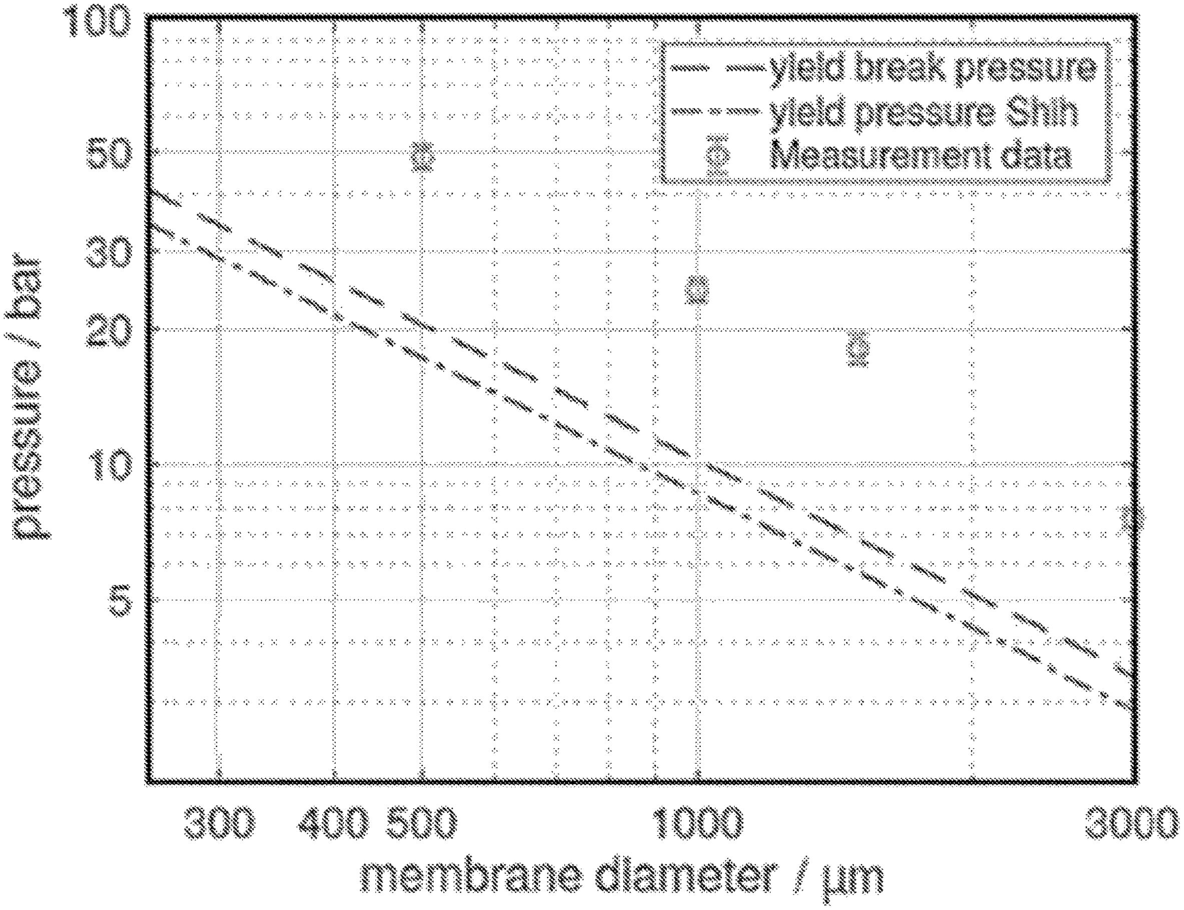
FIG. 12 is a chart showing the rupture pressure ratings of a heat rupturable membrane of an ingestible device according to illustrative embodiments.

Parylene membranes were rupture tested using a test stand, the results are plotted in FIG. 12. An inverse relationship between the rupture pressure and the membrane diameter was observed.

Parylene membranes with a thickness of 20 μm and diameter of 300 μm were observed to be sufficiently strong to retain more than 50 bar of static pressure. Furthermore the Inventors observed that the response time of such a rupturable membrane 108 may be as low as 50 ms. If flow restrictions became an issue with a 300 μm diameter membrane 108, it would possible to increase the diameter of membrane 108, however doing so may decrease the rupture strength and increase the response time of the valve. The selected battery was sufficiently powerful to power the heater 102 to melt membranes ranging from 200 μm to 500 m. For larger diameters, the inventors observed that the platinum conductor may melt before the parylene membrane 108, due to the quadratic increase in convective flux at the water-parylene interface (e.g., position 136).

The above-described embodiments of the technology described herein can be implemented in any of numerous ways. For example, the embodiments may be implemented using hardware, software or a combination thereof. When implemented in software, the software code can be executed on any suitable processor or collection of processors, whether provided as a single processor or multiple processors. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a processor readable storage medium (or multiple computer readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a processor readable storage medium may retain information for a sufficient time to provide processor-executable instructions in a non-transitory form. Such a processor readable storage medium or media can be transportable, such that the program or programs stored thereon can be loaded onto one or more different computing devices or other processors to implement various aspects of the present disclosure as discussed above. As used herein, the term " processor-readable storage medium" encompasses only a non-transitory processor-readable medium that can be considered to be a manufacture (i.e., article of manufacture) or a machine. Alternatively or additionally, the disclosure may be embodied as a processor readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for dispensing a material comprising:

a housing including a reservoir and an outlet, wherein the reservoir is configured to contain the material;

a heat rupturable membrane disposed within the housing and configured to selectively separate the reservoir from the outlet; and a heater thermally coupled to the heat rupturable membrane and thermally insulated from at least one of an environment surrounding the device and the reservoir, wherein a portion of the heater configured to generate heat extends at least partially around an opening the heat rupturable membrane extends across, wherein the portion of the heater that extends at least partially around the opening that the heat rupturable membrane extends across is a resistive portion.

2. The device of claim 1, wherein the housing includes a frame and the heater is disposed within the frame.

3. The device of claim 1, wherein the heater is generally horseshoe shaped such that the heat rupturable membrane forms a generally horseshoe shaped flap when ruptured by the heater.

4. The device of claim 1, wherein the device is configured such that the material flows from the reservoir to the outlet through an opening created in the heat rupturable membrane when the heater is actuated.

5. The device of claim 1, wherein the heater is configured to rupture the heat rupturable membrane when actuated.

6. The device of claim 1, wherein the material comprises at least one of a gas, a fluid, a viscous fluid, and an aerosolized powder.

7. The device of claim 1, wherein the material is pressurized within the reservoir.

8. The device of claim 1, further comprising a potential energy source configured to apply a pressure to the reservoir to dispense the material through the outlet.

9. The device of claim 8, wherein the potential energy source includes a compressed gas.

10. The device of claim 8, wherein the potential energy source includes a chemical mixing chamber.

11. The device of claim 8, wherein the potential energy source includes a hydraulic cylinder.

12. The device of claim 1, further comprising a power source electrically coupled to the heater such that the power source operates the heater to heat the heat rupturable membrane when the power source is actuated.

13. The device of claim 12, further comprising a processor configured to selectively actuate the power source to selectively rupture the heat rupturable membrane.

14. A thermally actuated valve comprising:

a frame;

a heat rupturable membrane disposed in an opening in the frame; and a heater disposed within the frame and thermally coupled to the heat rupturable membrane, wherein the heater is configured to rupture the heat rupturable membrane when actuated, wherein a portion of the heater configured to generate heat extends at least partially around the opening and the heat rupturable membrane extends across the opening, wherein the portion of the heater that extends at least partially around the opening that the heat rupturable membrane extends across is a resistive portion.

15. The thermally actuated valve of claim 14, further comprising a power source electrically coupled to the heater such that the power source operates the heater to heat the heat rupturable membrane when the power source is actuated.

16. The thermally actuated valve of claim 15, further comprising a processor configured to selectively actuate the power source to selectively rupture the heat rupturable membrane.

17. The thermally actuated valve of claim 14, wherein the thermally actuated valve is disposed within a housing, wherein the housing includes a reservoir and an outlet.

18. A method of dispensing a material, the method comprising:

heating a heat rupturable membrane with a heater thermally insulated from at least one of an external environment of a device and a reservoir of the device, wherein a portion of the heater configured to generate heat extends at least partially around an opening and the heat rupturable membrane extends across the opening, wherein the portion of the heater that extends at least partially around the opening that the heat rupturable membrane extends across is a resistive portion;

rupturing the heat rupturable membrane; and dispensing the material from the reservoir through an outlet of the device after the heat rupturable membrane is ruptured.

19. The method of claim 18, wherein heating the heat rupturable membrane includes resistively heating the heat rupturable membrane.

20. The method of claim 18, further comprising pressurizing the material within the reservoir of the device.

21. The method of claim 18, wherein dispensing the material includes actuating a potential energy source.

22. The method of claim 21, wherein actuating the potential energy source includes applying a pressure to the material.

* * * * *